US012685439B2

(12) United States Patent
    Lindgren

(10) Patent No.: US 12,685,439 B2
(45) Date of Patent: Jul. 21, 2026

(54) ELECTROPHYSIOLOGICAL STIMULATOR AND EVOKED RESPONSE SYSTEM AND METHOD

(71) Applicant: Evoq Technologies LLC, Henderson, NV (US)

(72) Inventor: Daniel Clay Lindgren, Henderson, NV (US)

(73) Assignee: EVOQ TECHNOLOGIES LLC, Henderson, NV (US)

( * ) Notice: Subject to any disclaimer, the term of this patent is extended or adjusted under 35 U.S.C. 154(b) by 680 days.

(21) Appl. No.: 17/961,321

(22) Filed: Oct. 6, 2022

(65) Prior Publication Data

US 2023/0114127 A1    Apr. 13, 2023

Related U.S. Application Data

(60) Provisional application No. 63/278,816, filed on Jan. 11, 2022, provisional application No. 63/253,510, filed on Oct. 7, 2021.

(51) Int. Cl.
    A61B 3/06 (2006.01)
    A61B 5/297 (2021.01)
    (Continued)

(52) U.S. Cl.
    CPC ............... A61B 3/06 (2013.01); A61B 5/398 (2021.01)

(58) Field of Classification Search
    CPC ........... A61B 3/06; A61B 5/398; A61B 5/297; A61B 5/315
    See application file for complete search history.

(56) References Cited

U.S. PATENT DOCUMENTS 9,554,721 B1    1/2017  Zikov et al.
11,109,795 B2    9/2021  Chester
            (Continued)

FOREIGN PATENT DOCUMENTS

CN        107049311 A    8/2017
EP         2314201 A1    4/2011
            (Continued)

OTHER PUBLICATIONS

PDF of Drawings for U.S. Appl. No. 63/130,156 (Year: 2020).*
            (Continued)

*Primary Examiner* — Justin Xu
(74) *Attorney, Agent, or Firm* — PATENT PORTFOLIO BUILDERS PLLC

(57)    ABSTRACT

A system includes a biosensor having at least one electrode to receive signals from a patient, an amplifier to receive the signals from the at least one electrode, an analog-to-digital converter to receive the signals from the amplifier and convert the signals to digital data, a microprocessor, and an antenna to transmit the digital data, and a mobile computing device to: illuminate at least one photostimulator of the mobile computing device to provide luminous stimulation to the patient and perform measurements associated with ocular/retinal functions of the patient, receive the digital data from the biosensor in response to the luminous stimulation, display a waveform associated with the measurements on a graphical user interface (GUI), perform a comparison between the measurements and a library of diagnostic images, and determine an evaluation of a retinal function of the patient based on the comparison.

23 Claims, 16 Drawing Sheets

(51) Int. Cl.

| | |
|---|---|
| *A61B 5/315* | (2021.01) |
| *A61B 5/398* | (2021.01) |

(56) References Cited

U.S. PATENT DOCUMENTS

| | | | |
|---|---|---|---|
| 2005/0131288 A1* | 6/2005 | Turner | A61B 5/4818 |
| | | | 128/903 |
| 2010/0234697 A1* | 9/2010 | Walter | A61B 5/4806 |
| | | | 600/301 |
| 2013/0242077 A1* | 9/2013 | Lin | A61B 3/113 |
| | | | 348/78 |
| 2015/0141763 A1 | 5/2015 | Roth et al. | |
| 2016/0183870 A1 | 6/2016 | Proud | |
| 2016/0270656 A1* | 9/2016 | Samec | A61B 5/1455 |
| 2020/0081247 A1* | 3/2020 | Khaderi | A61B 5/053 |
| 2021/0153736 A1 | 5/2021 | Palanker et al. | |
| 2021/0279874 A1* | 9/2021 | Boyd | A61B 3/14 |
| 2021/0393957 A1 | 12/2021 | Hamrah et al. | |
| 2022/0176123 A1* | 6/2022 | Allen | A61B 5/6821 |
| 2024/0049959 A1* | 2/2024 | Feola | A61B 3/0008 |

FOREIGN PATENT DOCUMENTS

| | | | |
|---|---|---|---|
| WO | 2017070372 A1 | 4/2017 | |
| WO | 2019052239 A1 | 3/2019 | |
| WO | 2020176947 A1 | 9/2020 | |
| WO | 2021072073 A1 | 4/2021 | |

OTHER PUBLICATIONS

PDF of Specification for U.S. Appl. No. 63/130,156 (Year: 2020).*

Yamashita et al., "A novel method to reduce noise in electroretinography using skin electrodes: a study of noise evel, inter-session variability, and reproducibility," International Ophthalmology, vol. 37, 2016.

Communication pursuant to Rules 70(2) and 70a(2) EPC in corresponding/related European Application No. 22879296.6, dated Aug. 12, 2025.

Cornish, E.E., et al., "The electroretinogram in the genomics era: outer retinal disorders," Eye, Jul. 7, 2021, vol. 35, No. 9, pp. 2406-2418, Nature Publishing Group.

Extended European Search Report in corresponding/related European Application No. 22879296, date of completion Jul. 14, 2025.

International Search Report in corresponding/related International Application No. PCT/US22/45917, date of mailing Jan. 31, 2023.

Written Opinion of the International Searching Authority in corresponding/related International Application No. PCT/US22/45917, date of mailing Jan. 31, 2023.

First Examination Report issued in corresponding/related Indian Patent Application No. 202417035879, issued Mar. 18, 2026.

Communication pursuant to Article 94(3) EPC in corresponding/related European Application No. 22879296.6, dated May 29, 2026.

* cited by examiner

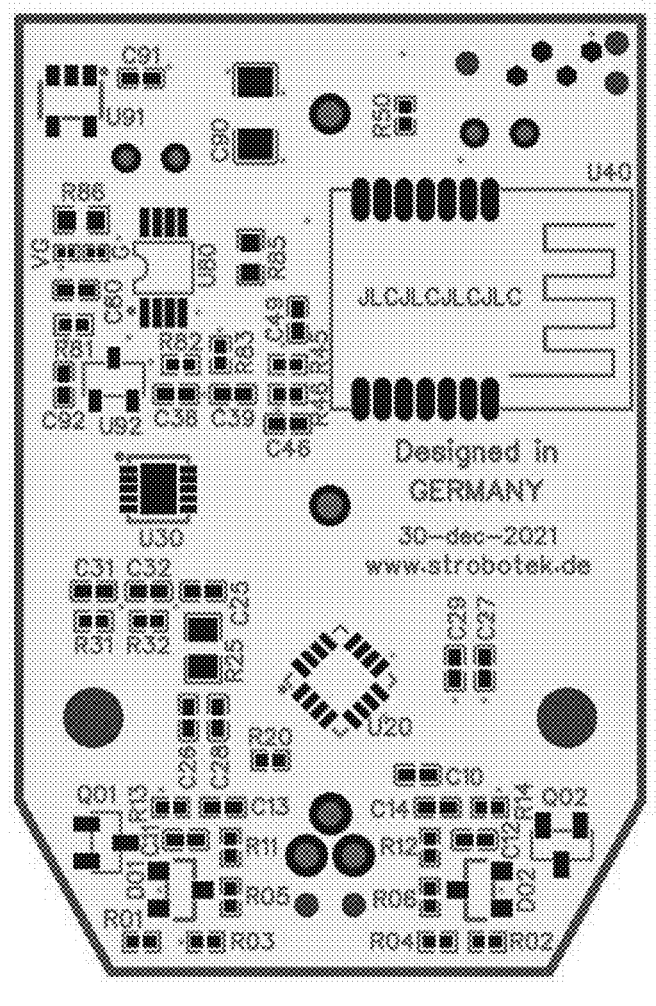
FIG. 5

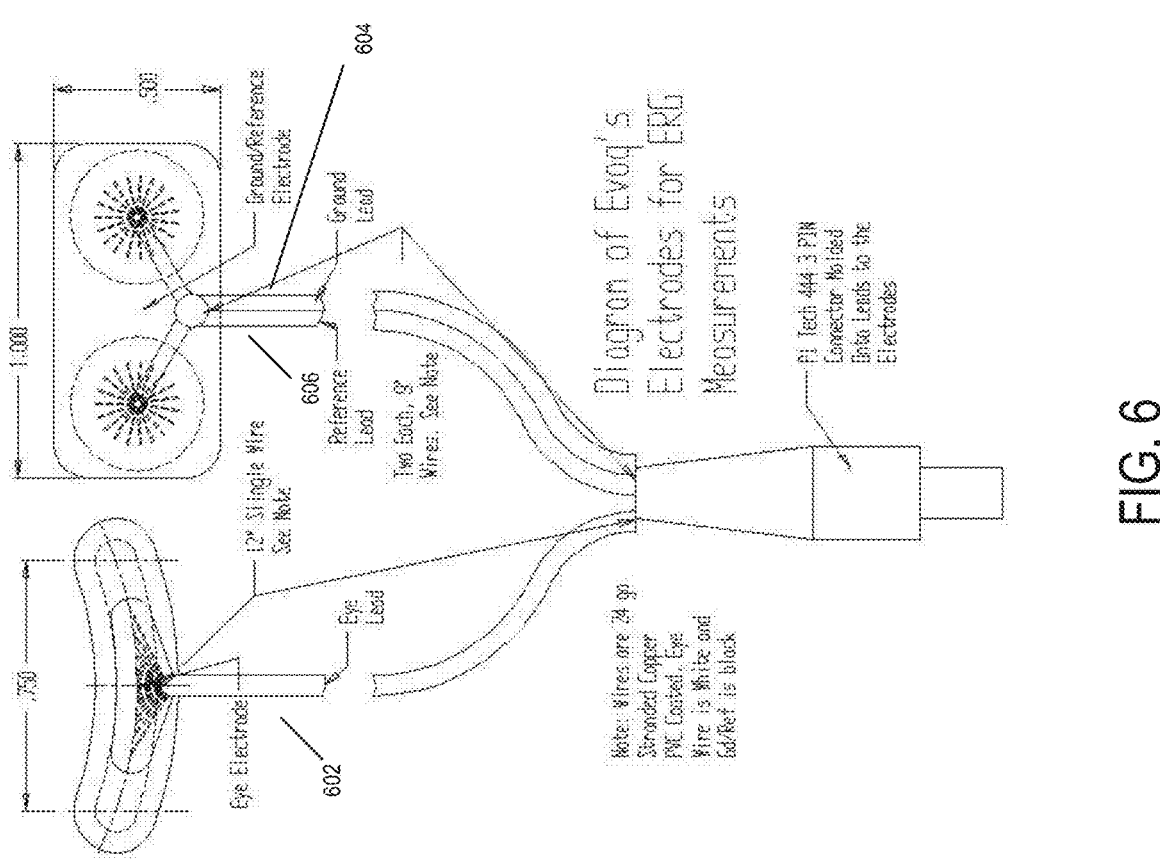
FIG. 6

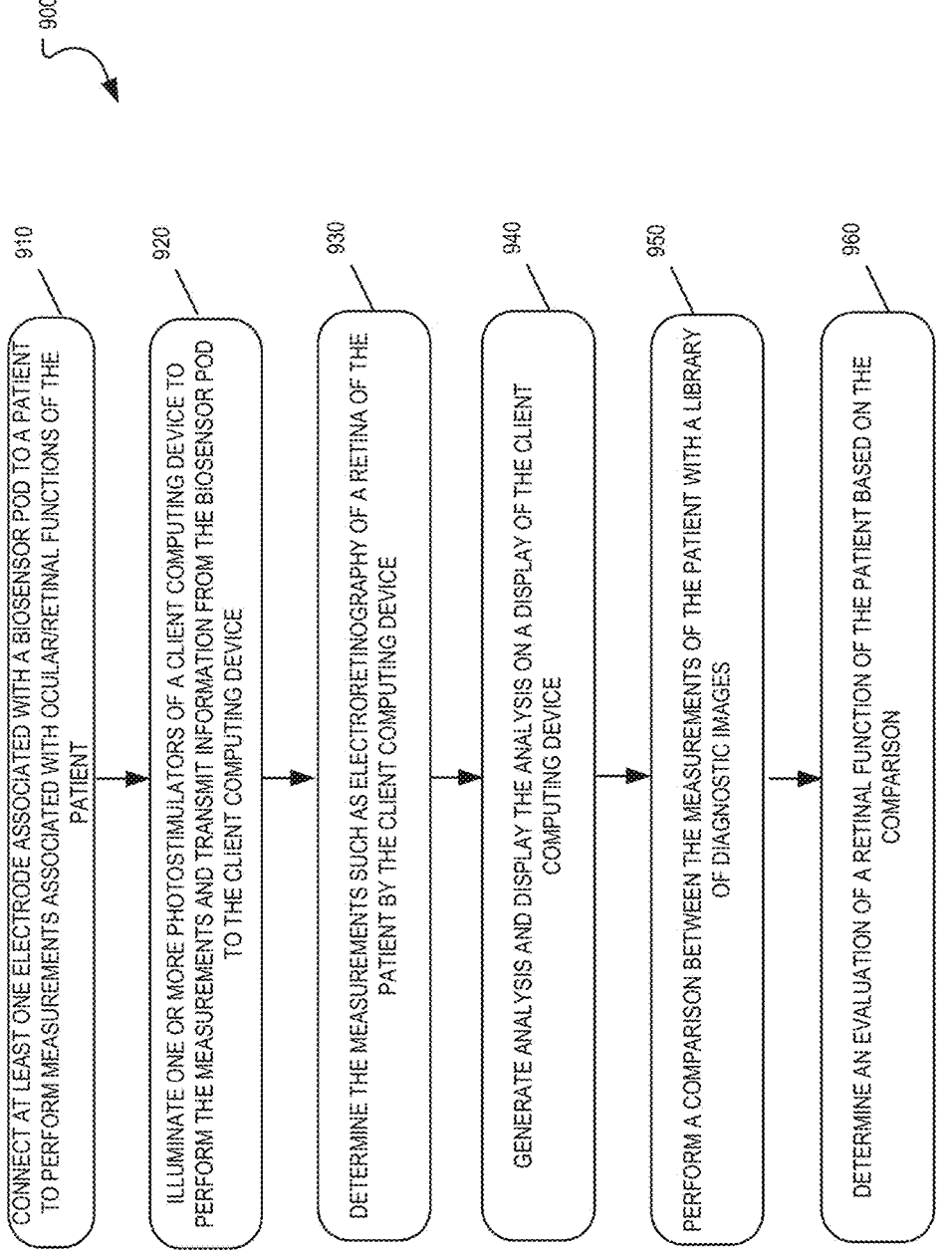

900

910 — CONNECT AT LEAST ONE ELECTRODE ASSOCIATED WITH A BIOSENSOR POD TO A PATIENT TO PERFORM MEASUREMENTS ASSOCIATED WITH OCULAR/RETINAL FUNCTIONS OF THE PATIENT

920 — ILLUMINATE ONE OR MORE PHOTOSTIMULATORS OF A CLIENT COMPUTING DEVICE TO PERFORM THE MEASUREMENTS AND TRANSMIT INFORMATION FROM THE BIOSENSOR POD TO THE CLIENT COMPUTING DEVICE

930 — DETERMINE THE MEASUREMENTS SUCH AS ELECTRORETINOGRAPHY OF A RETINA OF THE PATIENT BY THE CLIENT COMPUTING DEVICE

940 — GENERATE ANALYSIS AND DISPLAY THE ANALYSIS ON A DISPLAY OF THE CLIENT COMPUTING DEVICE

950 — PERFORM A COMPARISON BETWEEN THE MEASUREMENTS OF THE PATIENT WITH A LIBRARY OF DIAGNOSTIC IMAGES

960 — DETERMINE AN EVALUATION OF A RETINAL FUNCTION OF THE PATIENT BASED ON THE COMPARISON

FIG. 9

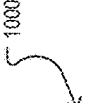
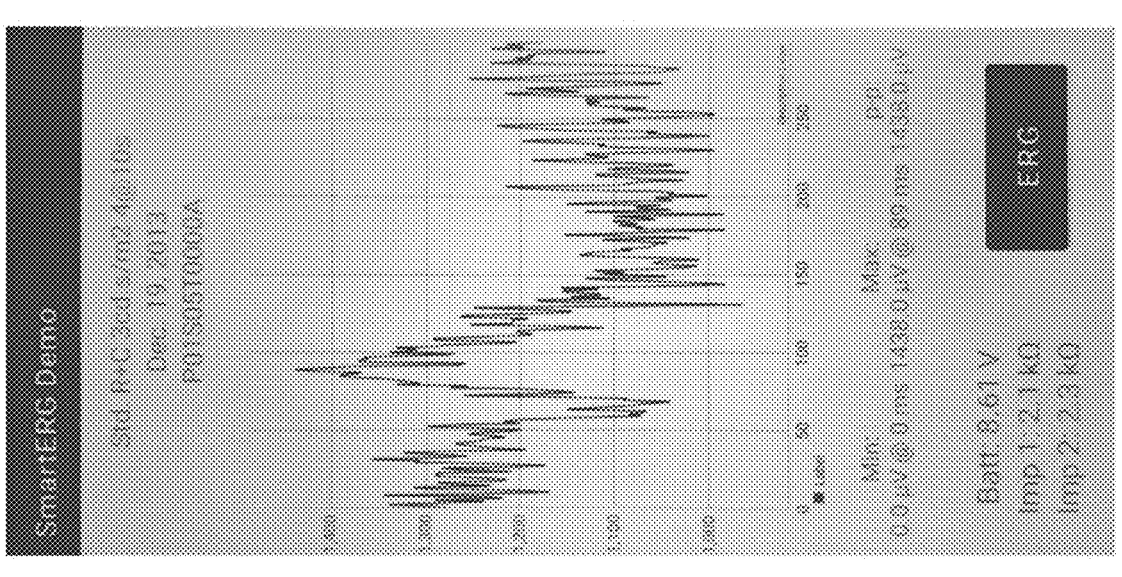
FIG. 10

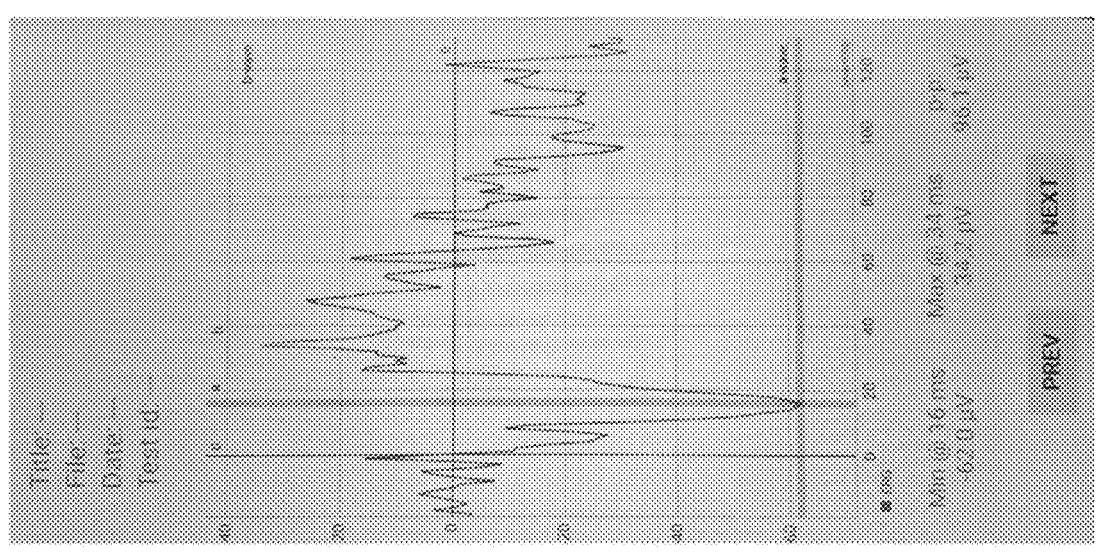
FIG. 11

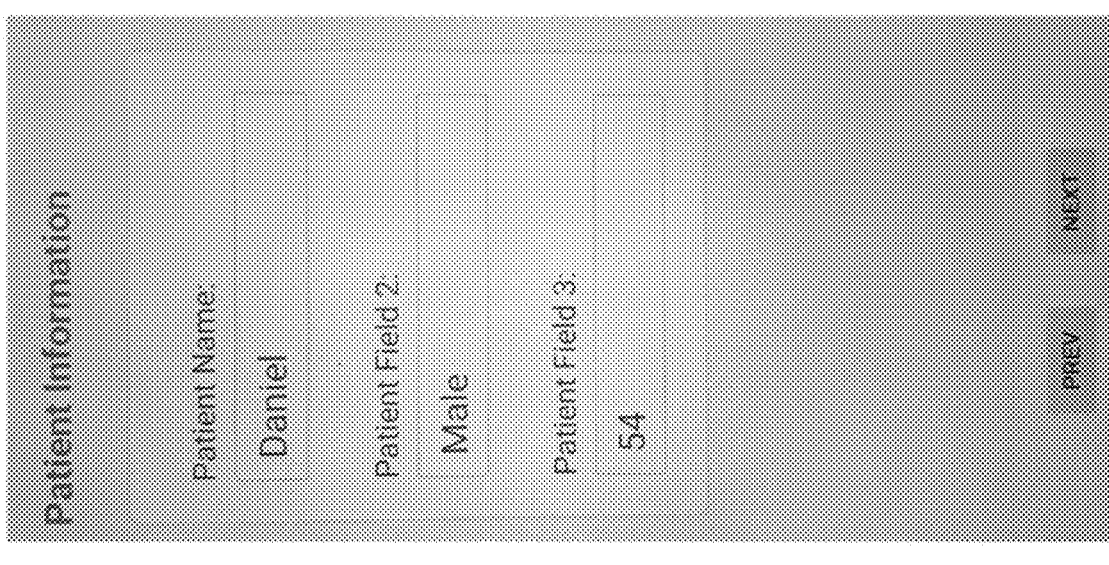
FIG. 12

ELECTROPHYSIOLOGICAL STIMULATOR AND EVOKED RESPONSE SYSTEM AND METHOD

CROSS REFERENCE TO RELATED APPLICATIONS

This application is related to and claims priority under 35 U.S.C. § 119 (e) to U.S. Patent Application No. 63/253,510, filed Oct. 7, 2021, entitled "Electrophysiological Test Unit," and U.S. Patent Application No. 63/278,816, filed Jan. 11, 2022, entitled "Evoked responses of vision, auditory, and somatosensory acquisition via wireless biosensor to smartphone and equivalent devices," the entire contents of which are incorporated herein by reference.

BACKGROUND

Conventional devices to test ocular or retinal function have been large and bulky. Additionally, conventional devices to evaluate a person's nervous system or acoustic response are also large, bulky, and unwieldy. The devices typically require extensive setup and have to be wired together with a number of interconnecting cables.

The conventional retinal and vision testing devices using electrophysiology have typically been desktop based personal computer systems with peripherals to evoke and capture the patient's response to various stimuli, namely light in the form of a flash or as a geometry pattern projection. The parameters of the stimulus are controlled by the computer and related software. The stimulator in conventional devices are fixed and require the patient to position him/herself to the machine. The larger conventional systems are prone to ambient electrical noise interference which very often required specialized rooms to block electrical noise that are required with these systems. The conventional devices have technically complex equipment and user interfaces, such that typical users have advanced education, to the level of M.D. or Ph.D. in ophthalmology. The conventional devices are also standalone data acquisition points in healthcare with no means to aggregate data and conduct global analysis of electrophysiological data.

It is with these issues in mind, among others, that various aspects of the disclosure were conceived.

SUMMARY

The present disclosure is directed to an electrophysiological stimulator and evoked response system and method. A system may include a client computing device that communicates with a BioSensor POD device to obtain measurement information and data associated with ocular/retinal functions of a patient. In one example, the BioSensor POD device may communicate with the client computing device using BLUETOOTH Low Energy (BLE) or another wireless network. One or more electrodes of the BioSensor POD device may be connected with the patient. One or more illuminating devices or photostimulators of the client computing device may be illuminated to produce a response in the patient including measurement data and information. The BioSensor POD device may communicate information and data associated with the response to the client computing device. The client computing device may display a representation of the information and data on a graphical user interface (GUI) of the client computing device. In addition, the client computing device may compare the information and data with a library of diagnostic images. The client computing device may determine an evaluation of a retinal function of the patient based on the comparison.

In one example, a system may include a biosensor comprising at least one electrode to receive signals from a patient, an amplifier to receive the signals from the at least one electrode, an analog-to-digital converter to receive the signals from the amplifier and convert the signals to digital data, a microprocessor, and an antenna to transmit the digital data, and a mobile computing device having a memory storing computer-readable instructions, and at least one processor to execute the instructions to illuminate at least one photostimulator of the mobile computing device to provide luminous stimulation to the patient and perform measurements associated with ocular/retinal functions of the patient, receive the digital data from the biosensor in response to the luminous stimulation, display a waveform associated with the measurements on a graphical user interface (GUI), perform a comparison between the measurements and a library of diagnostic images, and determine an evaluation of a retinal function of the patient based on the comparison.

In another example, a method may include illuminating, by at least one processor of a mobile computing device, at least one photostimulator of the mobile computing device to provide luminous stimulation to a patient and perform measurements associated with ocular/retinal functions of the patient, receiving, by at least one electrode of a biosensor, signals from the patient, receiving, by an amplifier of the biosensor, the signals from the at least one electrode, receiving, by an analog-to-digital converter of the biosensor, the signals from the amplifier and converting the signals to digital data, transmitting, by an antenna of the biosensor, the digital data to the mobile computing device, receiving, by the at least one processor of the mobile computing device, the digital data from the biosensor in response to the luminous stimulation, displaying, by the at least one processor of the mobile computing device, a waveform associated with the measurements on a graphical user interface (GUI), performing, by the at least one processor of the mobile computing device, a comparison between the measurements and a library of diagnostic images, and determining, by the at least one processor of the mobile computing device, an evaluation of a retinal function of the patient based on the comparison.

In another example, a non-transitory computer-readable storage medium includes instructions stored thereon that, when executed by a mobile computing device cause the mobile computing device to perform operations, the operations including illuminating at least one photostimulator of the mobile computing device to provide luminous stimulation to a patient and perform measurements associated with ocular/retinal functions of the patient, receiving, by at least one electrode of a biosensor, signals from the patient, receiving, by an amplifier of the biosensor, the signals from the at least one electrode, receiving, by an analog-to-digital converter of the biosensor, the signals from the amplifier and converting the signals to digital data, transmitting, by an antenna of the biosensor, the digital data to the mobile computing device, receiving the digital data from the biosensor in response to the luminous stimulation, displaying a waveform associated with the measurements on a graphical user interface (GUI), performing a comparison between the measurements and a library of diagnostic images, and determining an evaluation of a retinal function of the patient based on the comparison.

These and other aspects, features, and benefits of the present disclosure will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 5 is a diagram of a printed circuit board of the BioSensor POD device according to an example of the instant disclosure.

FIG. 6 is a diagram of an ERG electrode assembly of the electrophysiological stimulator and evoked response system according to an example of the instant disclosure.

FIG. 9 is a flowchart of a method of performing measurements associated with ocular/retinal functions of a patient according to an example of the instant disclosure.

FIGS. 10-12 show example screenshots of a graphical user interface (GUI) of the evoked response application according to an example of the instant disclosure.

DETAILED DESCRIPTION

Figure 1:
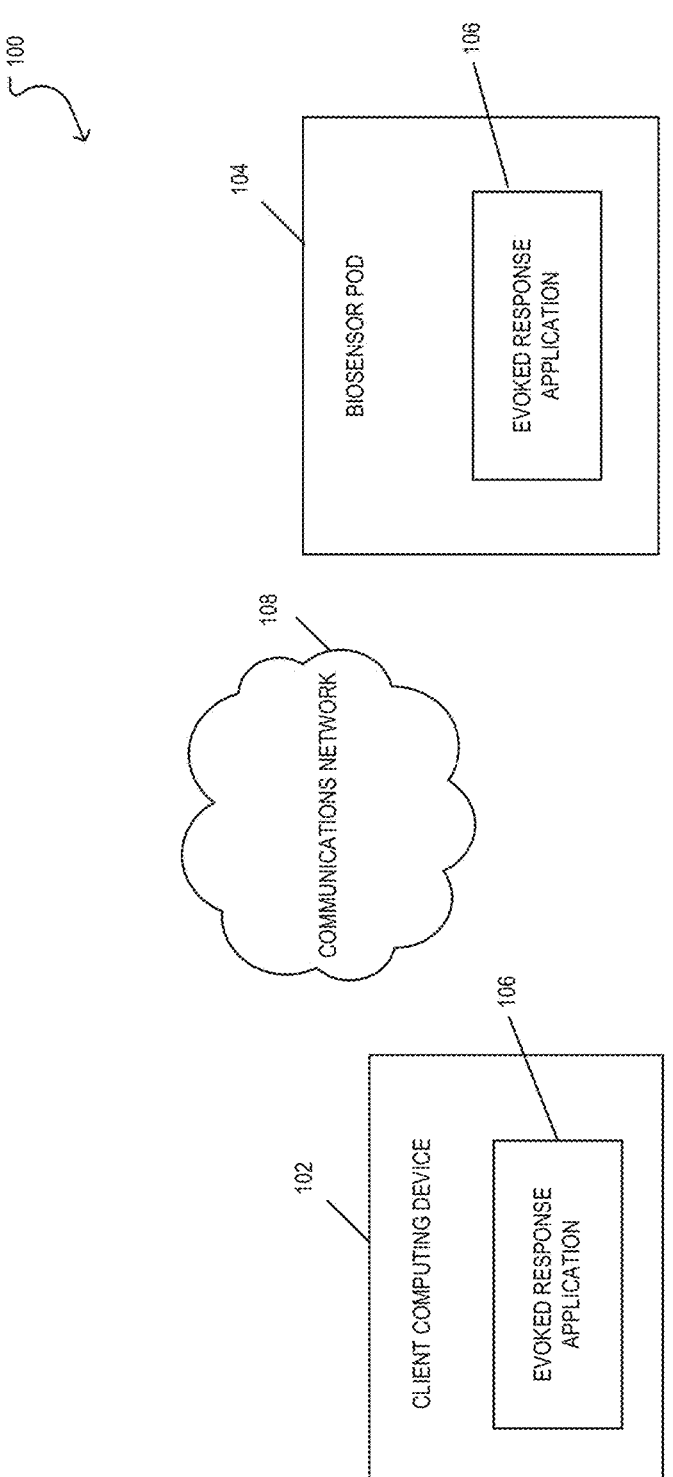
FIG. 1 is a block diagram of an electrophysiological stimulator and evoked response system according to an example of the instant disclosure.

The present invention is more fully described below with reference to the accompanying figures. The following description is exemplary in that several embodiments are described (e.g., by use of the terms "preferably," "for example," or "in one embodiment"); however, such should not be viewed as limiting or as setting forth the only embodiments of the present invention, as the invention encompasses other embodiments not specifically recited in this description, including alternatives, modifications, and equivalents within the spirit and scope of the invention. Further, the use of the terms "invention," "present invention," "embodiment," and similar terms throughout the description are used broadly and not intended to mean that the invention requires, or is limited to, any particular aspect being described or that such description is the only manner in which the invention may be made or used. Additionally, the invention may be described in the context of specific applications; however, the invention may be used in a variety of applications not specifically described.

The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted. Further, the description is not to be taken in a limiting sense, but is made merely for the purpose of illustrating the general principles of the invention, since the scope of the invention is best defined by the appended claims.

It will be understood that, although the terms "first," "second," etc. may be used herein to describe various elements, these elements should not be limited by these terms. These terms are only used to distinguish one element from another. Purely as a non-limiting example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an," and "the" are intended to include the plural forms as well, unless the context clearly indicates otherwise. It should also be noted that, in some alternative implementations, the functions and/or acts noted may occur out of the order as represented in at least one of the several figures. Purely as a non-limiting example, two figures shown in succession may in fact be executed substantially concurrently or may sometimes be executed in the reverse order, depending upon the functionality and/or acts described or depicted.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Aspects of an electrophysiological stimulator and evoked response system includes a client computing device such as a mobile computing device that communicates with a Bio-Sensor component also known as a POD. As an example, the client computing device may communicate with the Bio-Sensor component using wireless communication such as BLUETOOTH. The POD may provide an interface that obtains evoked responses to one or more light flashes from a retina of a subject's eye. As an example, the POD may have one or more electrodes that may be attached to an eye or attached near an eye to be evaluated, a low level, low noise electronic signal conditioner and digitizer, and a wireless communications interface to send information and data to the client computing device.

In one example, the system may include a biosensor comprising at least one electrode to receive signals from a patient, an amplifier to receive the signals from the at least one electrode, an analog-to-digital converter to receive the signals from the amplifier and convert the signals to digital data, a microprocessor, and an antenna to transmit the digital data, and a mobile computing device having a memory storing computer-readable instructions, and at least one processor to execute the instructions to illuminate at least one photostimulator of the mobile computing device to provide luminous stimulation to the patient and perform measurements associated with ocular/retinal functions of the patient, receive the digital data from the biosensor in response to the luminous stimulation, display a waveform associated with the measurements on a graphical user interface (GUI), perform a comparison between the measurements and a library of diagnostic images, and determine an evaluation of a retinal function of the patient based on the comparison.

The electrophysiological stimulator and evoked response system may include an electrophysiological stimulator and evoked response sensor device, also known as an ESEFS device or a BioSensor. The ESEFS may include a number of components that may allow a user to perform a diagnostic evaluation and record associated results with one of a number of different body functions. As an example, the ESEFS may obtain information and measurements associated with ocular/retinal functions such as electroretinography including full-field flash ERG, e.g., ffERG, pattern ERG, e.g., pERG, multi-focal ERG, e.g., mfERG, electro-oculogram, e.g., EOG, and dark adaptation impairment, e.g., DAI, among others. In some applications, a patient's nervous system may be evaluated using testing of the somatosensory system using neural response imaging and neural response measurements.

In addition, the evaluation may include determining a patient's acoustic system response with testing that includes audio evoked potentials (AEP), auditory brainstem response (ABR), and brainstem auditory evoked potentials (BAEP). The ESEFS device may perform measurements to determine ocular/retinal disorders using electroretinography. The ESEFS measurements may be electroretinography, e.g., an ERG. As is known, an ERG may be a diagnostic test that measures electrical activity of the retina in response to a light stimulus. The ESEFS may also perform additional functions.

As an example, the system may include one or more computing devices such as a mobile computing device. The mobile computing device may be a smartphone and may have an evoked response application that is executed by the mobile computing device. In one example, the mobile computing device may have one or more image capturing devices as well as one or more flash devices. The mobile computing device may illuminate one or more flash devices to obtain measurements associated with ocular/retina activity of a patient. The flash devices may perform illuminance stimulation associated with an ERG test. Additionally, the system may include a BioSensor device or a POD. The POD may include hardware devices including a low noise input amplifier that may condition signals obtained from patient connected electrodes to an amplitude sufficient to allow their digitization by a sixteen bit analog to digital converter, e.g., an ADC. Additionally, the POD may include one or more microprocessors such as a Cortex M4 microprocessor device having input and output as well as RAM. The M4 device may further have networking capabilities such as a BLUETOOTH transceiver. Additionally, the POD may have an ERG electrode assembly that may connect amplifier input to a patient to be tested and may provide electronic signals associated with the ERG test. As a result, the system may utilize the client computing device and the POD to perform a retinographic examination of a patient's eyes/retinas.

The system discussed herein provides electrophysiological stimulation and evoked response units and methods of performing the stimulation and evoked response. As an example, the system includes electroretinography units that can evaluate eyes/retinas of a subject. The system further provides other types of analysis associated with particular stimuli and evoked responses.

As an example, the system may include an electrophysiological unit including a client computing device that wirelessly communicates data and control signals with a Bio-Sensor POD that can include one or more electrodes as well as other sensing elements that may be in communication with a patient or subject. The client computing device may be a smartphone or another mobile computing device such as a tablet computing device that may include an evoked response application. The evoked response application may provide data analysis of information obtained by the Bio-Sensor POD and may display an interface such as a graphical user interface (GUI) on a display of the client computing device. The client computing device also may have one or more devices to provide luminous stimulation such as photostimulators. The BioSensor POD may be powered by a battery such as a lithium ion or a coin battery. The client computing device may have one or more photostimulators such as flash devices that provide with illumination associated with one or more imaging devices or cameras of the client computing device.

The system may provide physiological function evaluation that may include electroretinography using a weaker flash in a dark-adapted eye of a subject. The system may provide physiological function evaluation that may include electroretinography using a stronger flash in a dark-adapted eye of the subject. The system may further provide retinal function evaluation including oscillatory potential measurement in an eye of the subject using utilization of the evoked response application. Additionally, the system may provide physiological function evaluation that may include electroretinography to a stronger flash in a light-adapted eye of the subject. The system may provide physiological function evaluation including electroretinography to a rapidly repeated stimulus in an eye of the subject. The system may provide physiological function evaluation including a user designed test of an eye of the subject. The system may further provide a retinal function evaluation using electroretinography in an eye of the subject. The system may compare data associated with the patient's eye with a library of diagnostic images that may be stored on the client computing device or in another location such as a cloud based database or network accessible database.

The system may perform a method of diagnosing a retinal disease for a subject believed to have a retinal disorder. As an example, the system may include an electrophysiological unit including a client computing device. The client computing device may have an evoked response application that may evaluate a retinal function of a subject and may conduct an evaluation of the subject's retinal function as well as diagnose whether there is a retinal disorder based on the evaluation of the retinal function. The evoked response application may be used to determine that there is a retinal disorder including one of Retinitis pigmentosa, Retinitis pigmestosa sine pigmento, Retinitis punctata albescens, Liber's congenital amaurosis, Choroideremia, Gyrate atophy of the retina and choroid, Goldman-Favre syndrome, Congenital stationary night blindness, X-linked juvenile retinoschisis, Achromatopsia, cone-rod dystrophies, and one or more disorders mimicking retinitis pigmentosa.

In one example, an electrode assembly of the system may include three wires that may be connected to the BioSensor using a three-pin connector. A first pin may be connected to an active electrode and may provide electrical connection to a cornea of an eye of the patient or with a lower eye lid. A second pin and a third pin may connect with a ground electrode and reference electrode providing electrical contact with a patient's left or right temple. The three electrodes may provide the client computing device with signals to record electroretinographs (ERGs) from the patient. Each of the ground and reference electrodes may be placed on a temple of the patient on either the left or right side of the face. The eye electrode may be placed in contact with the face of the patient below the patient's eye. The electrode assembly may have the leads that are compact to minimize tension between the BioSensor connector and the electrodes. The wire leads may have a particular color such as black and/or white to ease in identification, placement, and allow for easier trouble shooting in a darkened laboratory setting.

Additionally, the system may be used to determine and evaluate other tests including audio evoked potentials (AEP), auditory brainstem response (ABR), brainstem auditory evoked potentials (BAEP), neural response imaging (NRI), and neural response measurements (NRM), among others.

In one example, the system may provide data acquisition and processing of electrophysiology for vision, auditory, somatosensory, and other applications. The system may utilize one or more flashes or lighting devices associated with the client computing device using an intensity array and fixed value filters. The BioSensor POD may send communication information and data as a particular data packet to the client computing device.

The system may provide a biophotometer for dark adaptation impairment detection, a full-field flash ERG/VEP (ffEGR) providing a retinal/visual pathway diagnostic device, a pattern ERG/VEP (pERG) that can provide early detection, diagnosis, and monitoring of glaucoma by determining sensitivity of a retina ganglion cell, a multi-focal ERG (mfERG) for precise detection, diagnosis, and monitoring of retinal degeneration by determining regional retinal function, and electro-oculogram (EOG) to determine retina pigment epithelium abnormality detection for age-related macular degeneration.

The system may provide the biophotometer that provides the retina test for dark adaptation impairment. In addition, the system provides a full field flash ERG/VEP device to detect and diagnose many forms of retinal diseases that can lead to blindness. Even further, the system may include a photovoltaic sensor to monitor dark environmental stability and indicate timing of one or more flashes. In one example, the system may utilize the display of the client computing device to provide line/check stimuli. Timing may be synchronized by monitoring flashing and light shifts or direct indicators such as audio and/or non-audible chirps.

FIG. 1 is a block diagram of an electrophysiological stimulator and evoked response system 100 according to an example of the instant disclosure. As shown in FIG. 1, the system 100 may include at least one client computing device 102 as well as at least one BioSensor POD device 104. The BioSensor POD device 104 may be known as a biosensor, a biosensor device, or a BioSensor POD device herein. The client computing device 102 and the BioSensor device 104 may have an evoked response application 106. Additionally, there may be a server-side component of the evoked response application 106 as well as a client-side component of the evoked response application 106. The BioSensor POD device 104 and/or the client computing device 102 may be in communication with one or more server computing devices (not shown) that may provide a cloud computing component of the evoked response application 106.

The client computing device 102 and the BioSensor POD device 104 may have the evoked response application 106 that may be a component of an application and/or service executable by the at least one client computing device 102 and/or the BioSensor POD device 104. For example, the evoked response application 106 may be a single unit of deployable executable code or a plurality of units of deployable executable code. According to one aspect, the evoked response application 106 may include one or more components that may be a web application, a native application, and/or a mobile application (e.g., an app) downloaded from a digital distribution application platform that allows users to browse and download applications developed with mobile software development kits (SDKs) including the App Store and GOOGLE PLAY®, among others.

The electrophysiological stimulator and evoked response system 100 also may include a relational database management system (RDBMS) or another type of database management system such as a NoSQL database system that stores and communicates data from at least one database. The data stored in the at least one database may be associated with one or more users associated with the system as well as one or more patients associated with the system. The data stored in the database may include measurements associated with the one or more patients as well as an image library that may be used for comparisons between the measurements. Each patient may have images and data captured at a particular time such as an examination. Each user may have username/password information for use with the system.

The at least one client computing device 102 and the at least one BioSensor POD device 104 may be configured to receive data from and/or transmit data through a communication network 108. Although the client computing device 102 and the BioSensor POD device 104 are shown as a single computing device, it is contemplated each computing device may include multiple computing devices.

The communication network 108 can be the Internet, an intranet, or another wired or wireless communication network. For example, the communication network 106 may include a Mobile Communications (GSM) network, a code division multiple access (CDMA) network, $3^{rd}$ Generation Partnership Project (GPP) network, an Internet Protocol (IP) network, a wireless application protocol (WAP) network, a Wi-Fi network, a BLUETOOTH network, a BLUETOOTH Low Energy (BLE) network, an Infrared Technology (IR) network, a Radio Frequency (RF) network, an IEEE 802.15.4 Communications protocol network (e.g., Zigbee), a RS-232 Serial communication standard network, a WiMax network, a satellite communications network, or an IEEE 802.11 standards network, as well as various communications networks thereof. Other conventional and/or later developed wired and wireless networks may also be used.

The client computing device 102 may include at least one processor to process data and memory to store data. The processor processes communications, builds communications, retrieves data from memory, and stores data to memory. The processor and the memory are hardware. The memory may include volatile and/or non-volatile memory, e.g., a computer-readable storage medium such as a cache, random access memory (RAM), read only memory (ROM), flash memory, or other memory to store data and/or computer-readable executable instructions. In addition, the client computing device 102 further includes at least one communications interface to transmit and receive communications, messages, and/or signals.

The client computing device 102 could be a programmable logic controller, a programmable controller, a laptop computer, a smartphone, a personal digital assistant, a tablet computer, a standard personal computer, or another processing device. The client computing device 102 may include a display, such as a computer monitor, for displaying data and/or graphical user interfaces. The client computing device 102 may also include a Global Positioning System (GPS) hardware device for determining a particular location, an input device, such as one or more cameras or imaging devices having one or more illumination devices capable of providing one or more flashes or illumination, a keyboard or a pointing device (e.g., a mouse, trackball, pen, or touch screen) to enter data into or interact with graphical and/or other types of user interfaces. In an exemplary embodiment, the display and the input device may be incorporated together as a touch screen of the smartphone or tablet computer.

The BioSensor POD device 104 may include at least one processor to process data and memory to store data. As an example, the BioSensor POD device 104 may be one or more ARM CORTEX-M4 devices. The processor processes communications, builds communications, retrieves data from memory, and stores data to memory. The processor and the memory are hardware. The memory may include volatile and/or non-volatile memory, e.g., a computer-readable storage medium such as a cache, random access memory (RAM), read only memory (ROM), flash memory, or other memory to store data and/or computer-readable executable instructions. In addition, the BioSensor POD device 104 further includes at least one communications interface to transmit and receive communications, messages, and/or signals.

Figure 2:
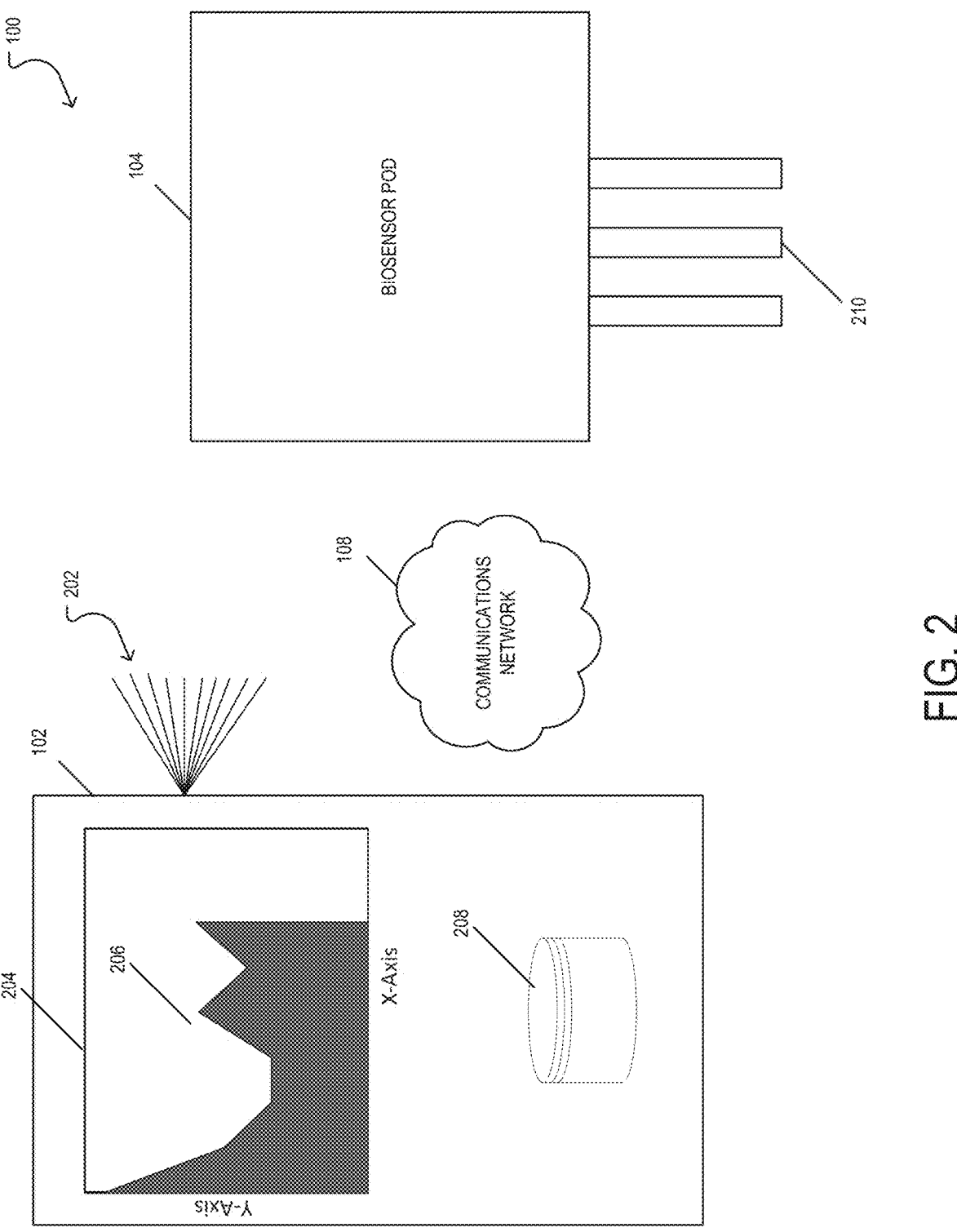
FIG. 2 is another block diagram of the electrophysiological stimulator and evoked response system according to an example of the instant disclosure.

FIG. 2 is another block diagram of the electrophysiological stimulator and evoked response system 100 according to an example of the instant disclosure. As shown in FIG. 2, the client computing device 102 may include one or more imaging devices that may provide one or more camera flashes by at least one photostimulator or illuminating device 202 such as by one or more light emitting diode (LED) devices. The at least one illuminating device 202 also may be associated with one or more flashlights provided by the client computing device 102. The at least one illuminating device 202 may be used to illuminate and cause a response in an eye/a retina of a patient. In addition, as shown in FIG. 2, a display 204 of the client computing device may be used to display a graphical user interface (GUI) provided by the evoked response application 106. The display 204 may be an organic light emitting diode (OLED) display and/or an LED display. Additionally, as shown in FIG. 2, the client computing device may include one or more storage devices that may store information associated with the evoked response application 106 that may include a library of diagnostic images 208. In another example, the library 208 may be stored on a server computing device and the client computing device 102 may obtain information associated with the library of diagnostic images 208 from the server computing device. As further shown in FIG. 2, the BioSensor POD device 104 may include one or more electrodes 210 that may be in communication with the patient and may obtain measurement data from the patient.

Figure 3:
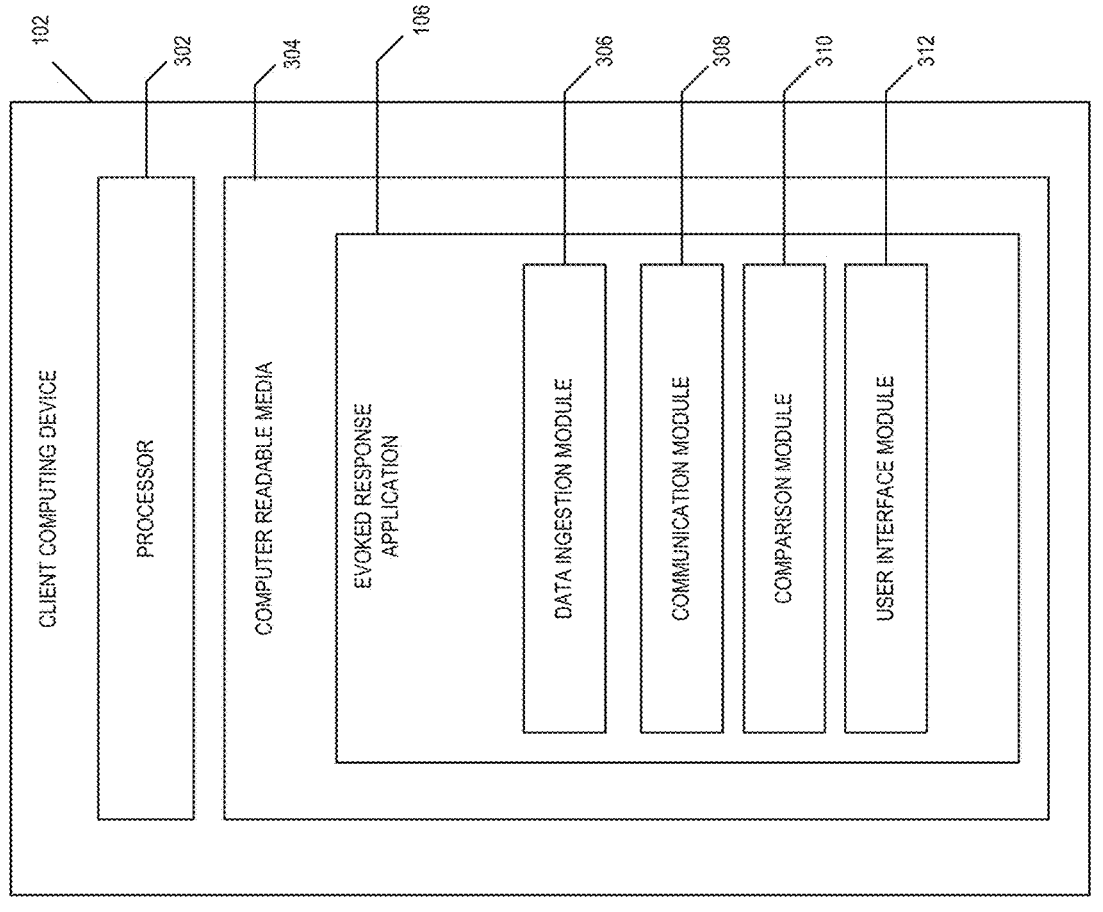
FIG. 3 is a block diagram of a client computing device of the electrophysiological stimulator and evoked response system having an evoked response application according to an example of the instant disclosure.

FIG. 3 illustrates a block diagram of the client computing device 102 according to an example embodiment. The client computing device 102 includes computer readable media (CRM) 304 in memory on which the evoked response application 106 or other user interface or application is stored. The computer readable media 304 may include volatile media, nonvolatile media, removable media, non-removable media, and/or another available medium that can be accessed by the processor 302. By way of example and not limitation, the computer readable media 304 comprises computer storage media and communication media. Computer storage media includes non-transitory storage memory, volatile media, nonvolatile media, removable media, and/or non-removable media implemented in a method or technology for storage of information, such as computer/machine-readable/executable instructions, data structures, program modules, or other data. Communication media may embody computer/machine-readable/executable instructions, data structures, program modules, or other data and include an information delivery media or system, both of which are hardware.

The evoked response application 106 may include a data ingestion module 306 for obtaining data and information associated with a patient. As an example, the data ingestion module 306 may be used to obtain measurement data from the BioSensor POD device 104 such as digital data associated with the one or more electrodes of the BioSensor POD device. In one example, the measurement data may be ocular/retinal data associated with the patient. The measurement data may be ERG data.

The evoked response application 106 may include a communication module 308 for communicating between the client computing device 102 and the BioSensor POD device 104. In one example, the client computing device 102 and the BioSensor POD device 104 may communicate using BLUETOOTH and may communicate information and data in a particular proprietary packet format. The data ingestion module 306 may receive the measurement data from the communication module 308 that is sent or transmitted from the BioSensor POD device 104 using the communication network 108 that can be a BLUETOOTH network or a BLUETOOTH Bluetooth Low Energy (BLE) network.

The evoked response application 106 may include a comparison module 310 for comparing measurement data associated with ocular/retinal functions with images that may be stored in a library of images that may be stored locally on the client computing device 102 and/or may be stored externally on a server computing device or in another location. The comparison data set will be unique in that a global database will be accumulated for a wide demographic set, therefore robust analysis and deep learning can be used to detect and diagnose pathophysiology. The comparison module 310 may provide feedback or analysis information based on the measurement data and may provide information such as retinal disorder information based on an evaluation of the retinal function of the patient. The comparison module 310 may perform one or more ERGs on the measurement data. In one example, the comparison module 310 may determine that the retinal disorder comprises at least one of Retinitis pigmentosa, Retinitis pigmentosa sine pigmento, Retinitis punctata albescens, Leber's congenital amaurosis, Choroideremia, Gyrate atrophy of the retina and choroid, Goldman-Favre syndrome, Congenital stationary night blindness, X-linked juvenile retinoschisis, Achromatopsia, cone-rod dystrophies, and at least one disorder mimicking retinitis pigmentosa.

In addition, the evoked response application 106 includes a user interface module 312 for displaying a user interface on the display. As an example, the user interface module 312 generates a native and/or web-based graphical user interface (GUI) that accepts input and provides output viewed by users of the client computing device 102 or another computing device. The client computing device 102 or another computing device may provide realtime automatically and dynamically refreshed information. The user interface module 312 may send data to other modules of the evoked response application 106 of the client computing device 102 and retrieve data from other modules of the evoked response application 106 of the client computing device 102 asynchronously without interfering with the display and behavior of the user interface displayed by the client computing device 102 or another computing device.

Figure 4:
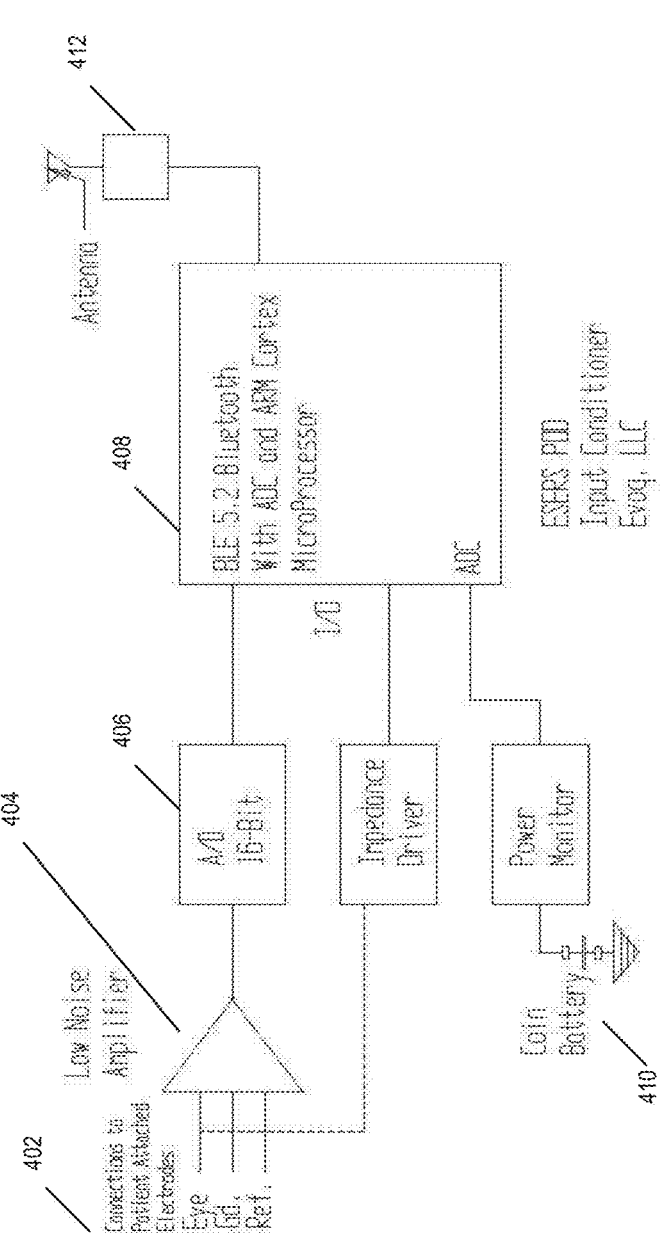
FIG. 4 is a block diagram of a BioSensor POD device of the electrophysiological stimulator and evoked response system according to an example of the instant disclosure.

FIG. 4 is a block diagram of a BioSensor POD of the electrophysiological stimulator and evoked response system according to an example of the instant disclosure. As shown in FIG. 4, the BioSensor POD may include one or more electrodes 402 including a first electrode that may be attached to a patient, a second electrode that may be a ground electrode, and a third electrode that may be a reference electrode. The one or more electrodes 402 may provide data and signals to a low noise amplifier 404 that is connected to a sixteen bit analog to digital converter 406, e.g., an ADC. The one or more electrodes 402 also may be connected to an impedance driver. The ADC 406 may provide the data and information to a microprocessor 408 that may be a BLE 5.2 microprocessor. The BioSensor POD 104 may be powered by one or more batteries 410 such as a coin battery that may have a power monitor. The BioSensor POD 104 may communicate to the client computing device 102 using an antenna 412 that may transmit and receive information.

FIG. 5 is a diagram 500 of a printed circuit board of the BioSensor POD device 104 according to an example of the instant disclosure.

FIG. 6 is a diagram 600 of an ERG electrode assembly of the electrophysiological stimulator and evoked response system 100 according to an example of the instant disclosure. In particular, FIG. 6 shows the one or more electrodes 402 including a first electrode 602 that may be an eye electrode, a second electrode 604 that may be a ground electrode, and a third electrode 606 that may be a reference electrode.

Figure 7:
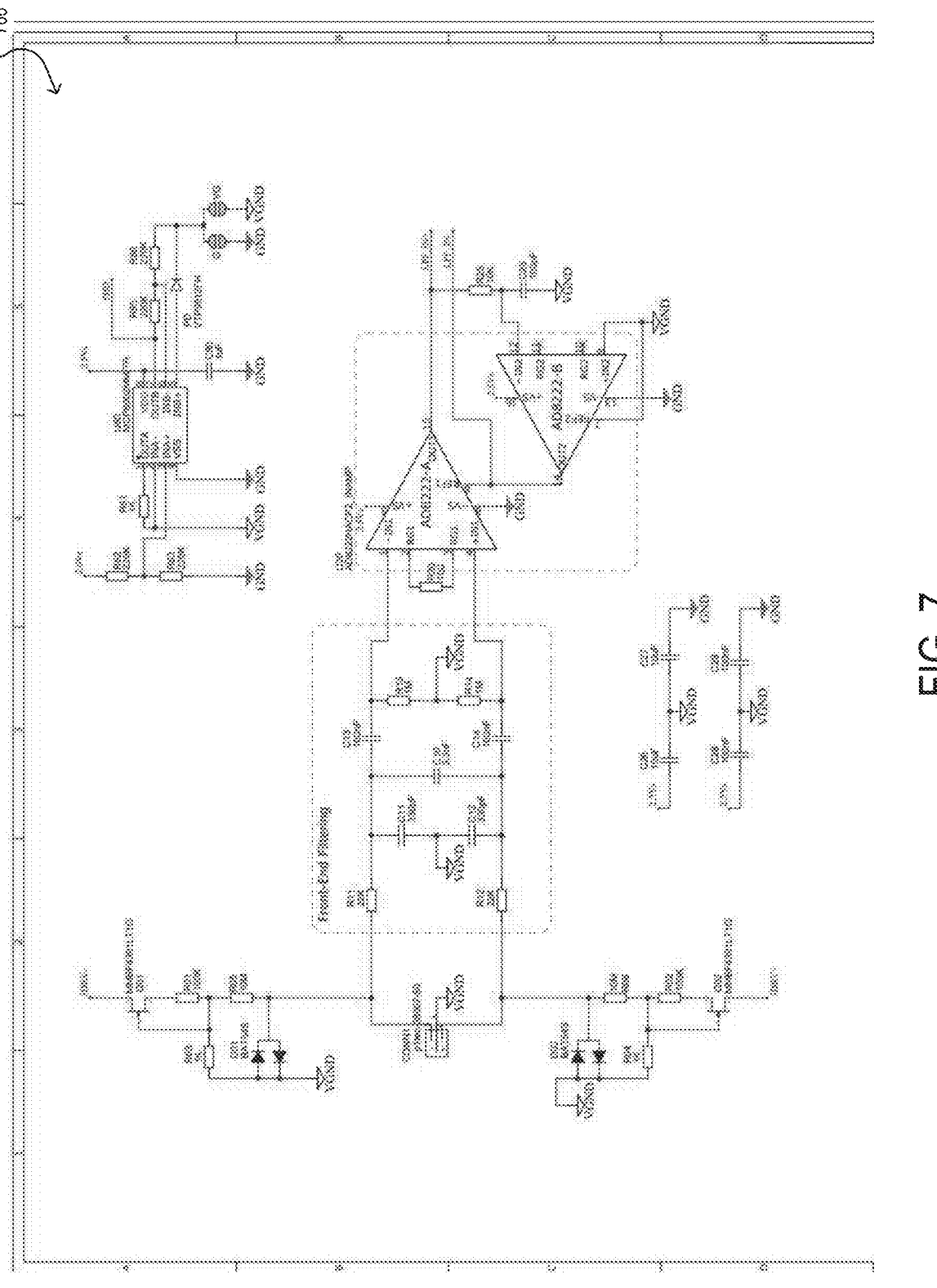
FIG. 7 is a first diagram of a circuit diagram of the BioSensor POD device according to an example of the instant disclosure.

FIG. 7 is a first diagram 700 of a circuit diagram of the BioSensor POD device 104 according to an example of the instant disclosure.

Figure 8:
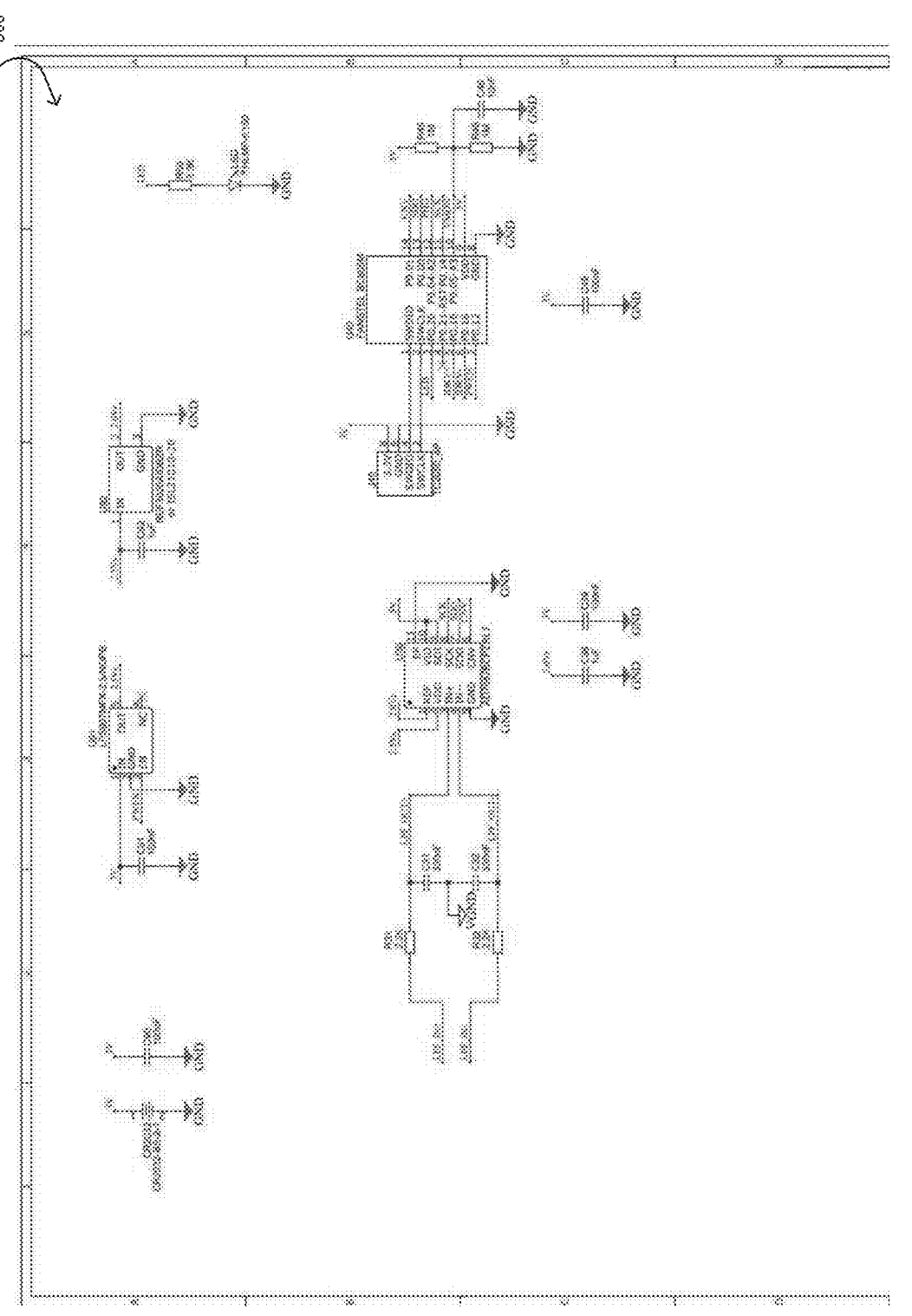
FIG. 8 is a second circuit diagram of the BioSensor POD device according to an example of the instant disclosure.

FIG. 8 is a second circuit diagram 800 of the BioSensor POD device 104 according to an example of the instant disclosure.

FIG. 9 illustrates an example method 900 of performing measurements associated with ocular/retinal functions of a patient according to an example of the instant disclosure. Although the example method 900 depicts a particular sequence of operations, the sequence may be altered without departing from the scope of the present disclosure. For example, some of the operations depicted may be performed in parallel or in a different sequence that does not materially affect the function of the method 900. In other examples, different components of an example device or system that implements the method 900 may perform functions at substantially the same time or in a specific sequence.

According to some examples, the method 900 may include connecting at least one electrode 402 associated with a BioSensor POD device 104 to a patient to perform measurements associated with ocular/retinal functions of the patient at block 910. As an example, the BioSensor POD device 104 may include at least one electrode 402 to receive signals from the patient, an amplifier 404 to receive signals from the at least one electrode 402, an analog-to-digital converter 406 to receive the signals from the amplifier 404 and convert the signals to digital data, a microprocessor 408, and an antenna 412 to transmit the digital data.

The at least one electrode 402 may include a first electrode 602 that makes electrical contact with the patient, a second electrode 604 that is a ground electrode, and a third electrode 606 that is a reference electrode.

The BioSensor POD device 104 may include a coin battery 410 to power the BioSensor POD device 104.

Next, according to some examples, the method 900 may include illuminating at least one photostimulator or illuminating device 202 of the mobile computing device 102 to provide luminous stimulation to the patient and perform measurements associated with ocular/retinal functions of the patient at block 920. The method 900 may further include receiving the digital data from the biosensor POD device 104 in response to the luminous stimulation.

Next, according to some examples, the method 900 may include determining the measurements of a retina of the patient by the mobile computing device 102 at block 930.

Next, according to some examples, the method 900 may include generating feedback or analysis and displaying the feedback or analysis on a display of the mobile computing device 102 at block 940. The feedback or analysis may include a waveform associated with the measurements that may be displayed on a graphical user interface (GUI).

Next, according to some examples, the method 900 may include performing a comparison between the measurements of the patient with a library of diagnostic images at block 950.

Next, according to some examples, the method 900 may include determining an evaluation of a retinal function of the patient based on the comparison at block 960.

In some examples, the measurements of the method 900 may include electroretinography in response to the luminous stimulation less than a particular threshold in a dark-adapted eye of the patient.

In some examples, the measurements of the method 900 may include electroretinography in response to the luminous stimulation greater than or equal to a particular threshold in a dark-adapted eye of the patient.

In some examples, the measurements of the method 900 may include electroretinography in response to the luminous stimulation greater than or equal to a particular threshold in a light-adapted eye of the patient.

In some examples, the measurements of the method 900 may include electroretinography in response to the luminous stimulation that is repeated.

In some examples, the measurements of the method 900 may be at least one of a full-field flash electroretinography (ERG), a pattern ERG, a multi-focal ERG, an electrooculogram, and dark adaptation impairment.

In some examples, the method 900 may include determining that the patient has a retinal disorder based on the evaluation of the retinal function of the patient. The retinal disorder may be at least one of Retinitis pigmentosa, Retinitis pigmentosa sine pigmento, Retinitis punctata albescens, Leber's congenital amaurosis, Choroideremia, Gyrate atrophy of the retina and choroid, Goldman-Favre syndrome, Congenital stationary night blindness, X-linked juvenile retinoschisis, Achromatopsia, cone and dystrophies, and at least one disorder mimicking retinitis pigmentosa.

In some examples, the method 900 may include the BioSensor POD device and the mobile computing device 102 communicating using BLUETOOTH Low Energy (BLE).

FIGS. 10-12 show example screenshots of a graphical user interface (GUI) of the evoked response application 106 according to an example of the instant disclosure.

As shown in FIG. 10, there is an example screenshot 1000 of an example GUI that shows feedback or analysis information based on the measurement data. There is a GUI element that can be selected to perform an ERG. As shown in FIG. 11, there is another example screenshot 1100 of an example GUI that shows feedback and analysis information based on the measurement data.

As shown in FIG. 12, there is an example screenshot 1200 of an example GUI that allows a user to enter patient or user information including a patient name, a patient sex (e.g., male/female), and a patient age, among other information.

Figure 13A:
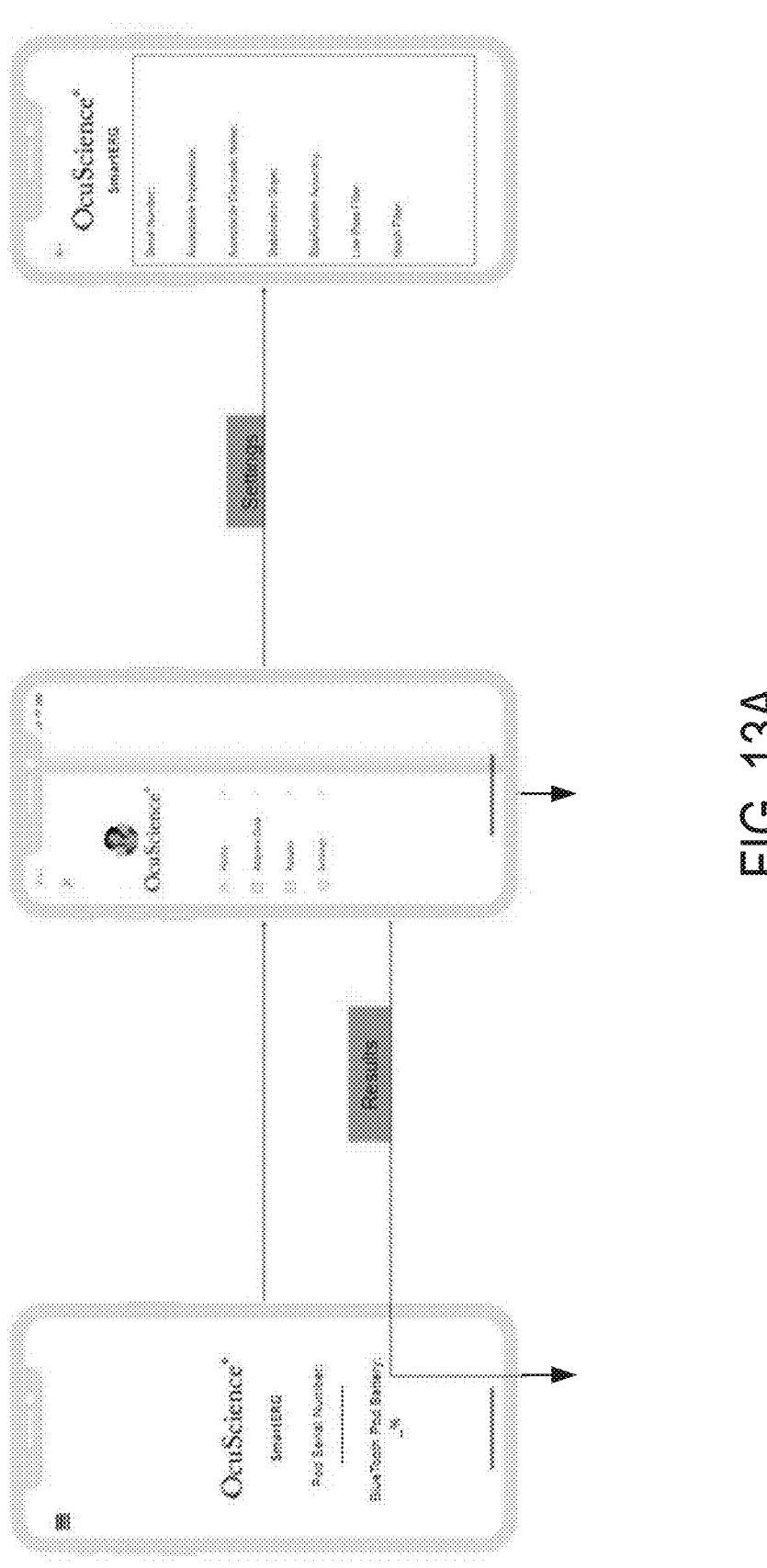
FIGS. 13A-13C show a user interaction diagram of the GUI of the evoked response application according to an example of the instant disclosure.
Figure 13B:
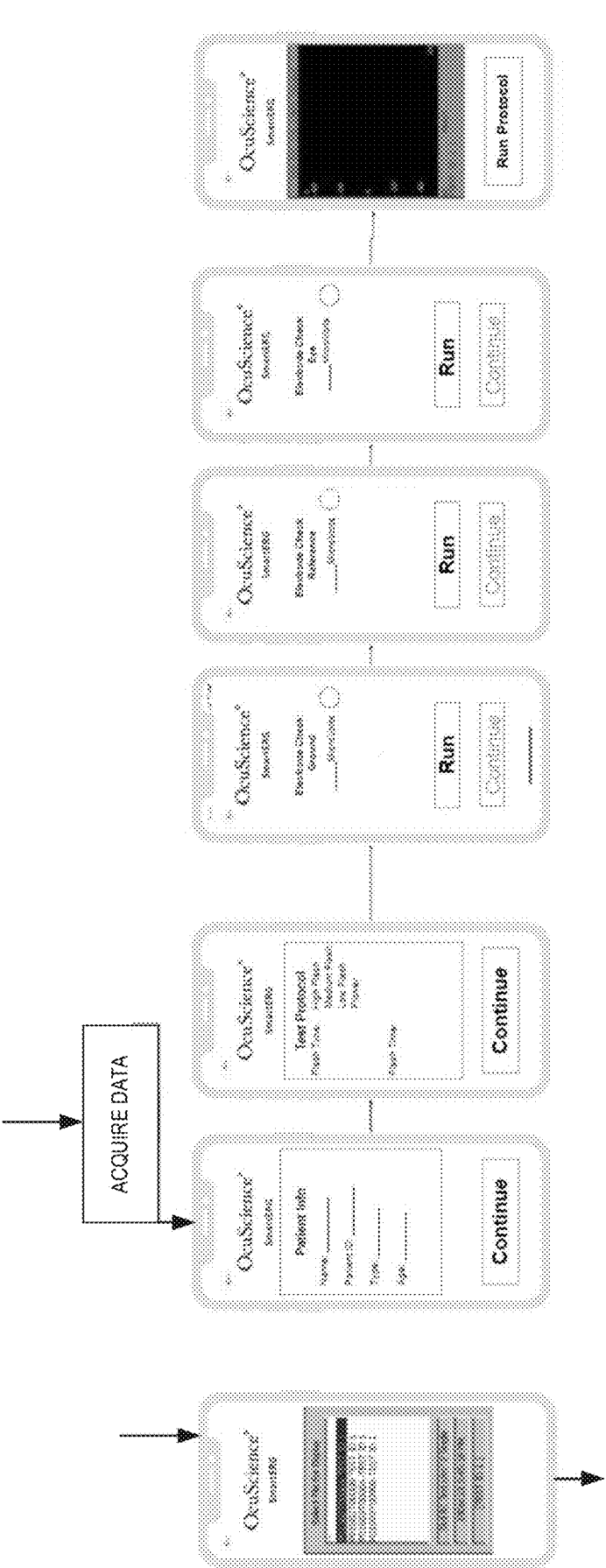
Figure 13C:
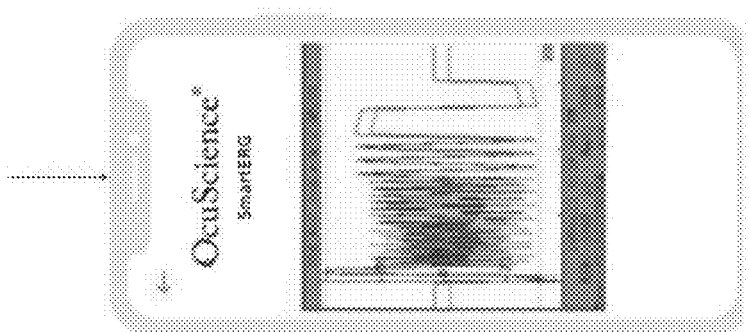

FIGS. 13A-13C show a user interaction diagram of the GUI of the evoked response application according to an example of the instant disclosure. As shown in FIG. 13A, a user can set up a number of settings associated with the system including providing a serial number, acceptable impedance, acceptable electrode noise, stabilization scope, stabilization accuracy, low pass filter information, and notch filter information. After setting up the settings as shown in FIG. 13A, the user can acquire data and determine results as shown in FIG. 13B. As shown in FIG. 13B, the user can provide patient information such as a name, a patient identifier, a patient type, and an age. The user can select a test protocol such as one of a high flash, a medium flash, a low flash, and a flicker as well as a flash time. The user may perform an electrode check for the ground electrode 604, the reference electrode 606, and the eye electrode 602 and then run the test protocol by selecting a test protocol button or GUI element. Example results are shown in FIG. 13C.

Figure 14:
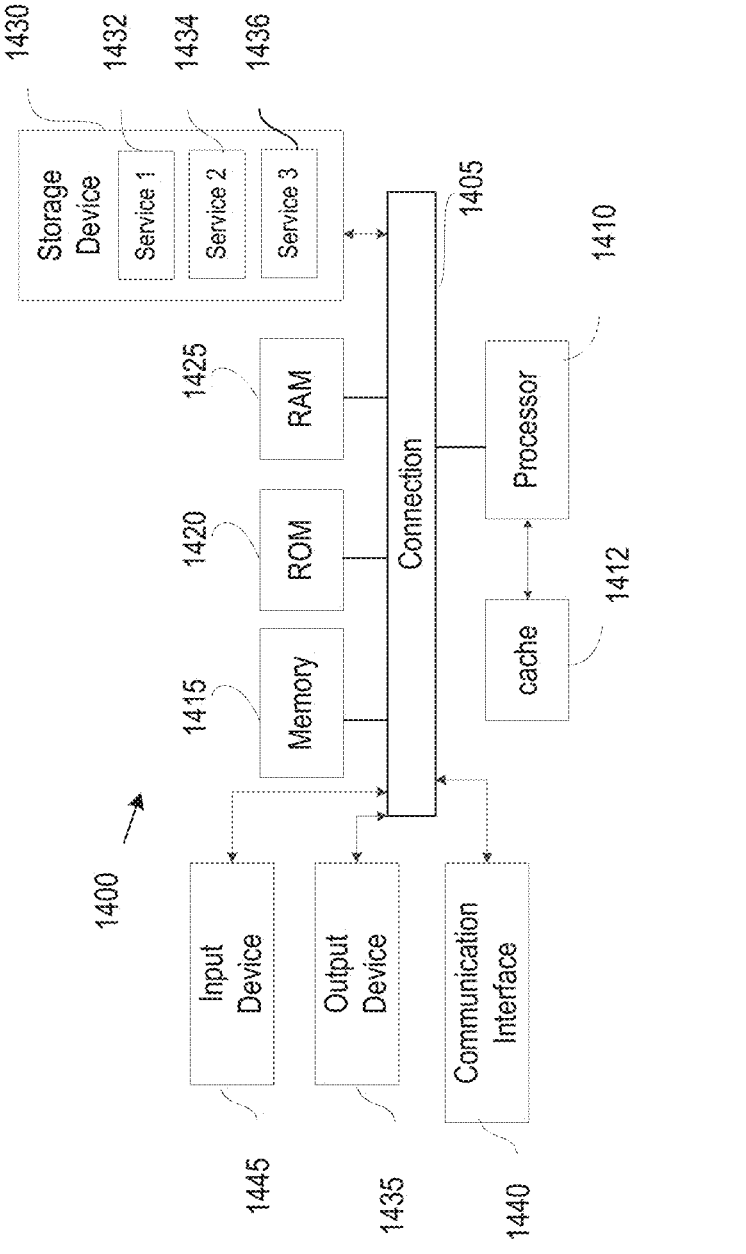
FIG. 14 shows an example of a system for implementing certain aspects of the present technology.

FIG. 14 shows an example of computing system 1400, which can be for example any computing device making up the computing device such as the client computing device 102, the BioSensor POD device 104, or any component thereof in which the components of the system are in communication with each other using connection 1405. Connection 1405 can be a physical connection via a bus, or a direct connection into processor 1410, such as in a chipset architecture. Connection 1405 can also be a virtual connection, networked connection, or logical connection.

In some embodiments, computing system 1400 is a distributed system in which the functions described in this disclosure can be distributed within a datacenter, multiple data centers, a peer network, etc. In some embodiments, one or more of the described system components represents many such components each performing some or all of the function for which the component is described. In some embodiments, the components can be physical or virtual devices.

Example system 1400 includes at least one processing unit (CPU or processor) 1410 and connection 1405 that couples various system components including system memory 1415, such as read-only memory (ROM) 1420 and random access memory (RAM) 1425 to processor 1410. Computing system 1400 can include a cache of high-speed memory 1412 connected directly with, in close proximity to, or integrated as part of processor 1410.

Processor 1410 can include any general purpose processor and a hardware service or software service, such as services 1432, 1434, and 1436 stored in storage device 1430, configured to control processor 1410 as well as a special-purpose processor where software instructions are incorporated into the actual processor design. Processor 1410 may essentially be a completely self-contained computing system, containing multiple cores or processors, a bus, memory controller, cache, etc. A multi-core processor may be symmetric or asymmetric.

To enable user interaction, computing system 1400 includes an input device 1445, which can represent any number of input mechanisms, such as a microphone for speech, a touch-sensitive screen for gesture or graphical input, keyboard, mouse, motion input, speech, etc. Computing system 1400 can also include output device 1435, which can be one or more of a number of output mechanisms known to those of skill in the art. In some instances, multimodal systems can enable a user to provide multiple types of input/output to communicate with computing system 1400. Computing system 1400 can include communications interface 1440, which can generally govern and manage the user input and system output. There is no restriction on operating on any particular hardware arrangement, and therefore the basic features here may easily be substituted for improved hardware or firmware arrangements as they are developed.

Storage device 1430 can be a non-volatile memory device and can be a hard disk or other types of computer readable media which can store data that are accessible by a computer, such as magnetic cassettes, flash memory cards, solid state memory devices, digital versatile disks, cartridges, random access memories (RAMs), read-only memory (ROM), and/or some combination of these devices.

The storage device 1430 can include software services, servers, services, etc., that when the code that defines such software is executed by the processor 1410, it causes the system to perform a function. In some embodiments, a hardware service that performs a particular function can include the software component stored in a computer-readable medium in connection with the necessary hardware components, such as processor 1410, connection 1405, output device 1435, etc., to carry out the function.

For clarity of explanation, in some instances, the present technology may be presented as including individual functional blocks including functional blocks comprising devices, device components, steps or routines in a method embodied in software, or combinations of hardware and software.

Any of the steps, operations, functions, or processes described herein may be performed or implemented by a combination of hardware and software services or services, alone or in combination with other devices. In some embodiments, a service can be software that resides in memory of a client device and/or one or more servers of a content management system and perform one or more functions when a processor executes the software associated with the service. In some embodiments, a service is a program or a collection of programs that carry out a specific function. In some embodiments, a service can be considered a server. The memory can be a non-transitory computer-readable medium.

In some embodiments, the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer-readable media. Such instructions can comprise, for example, instructions and data which cause or otherwise configure a general purpose computer, special purpose computer, or special purpose processing device to perform a certain function or group of functions. Portions of computer resources used can be accessible over a network. The executable computer instructions may be, for example, binaries, intermediate format instructions such as assembly language, firmware, or source code. Examples of computer-readable media that may be used to store instructions, information used, and/or information created during methods according to described examples include magnetic or optical disks, solid-state memory devices, flash memory, USB devices provided with non-volatile memory, networked storage devices, and so on.

Devices implementing methods according to these disclosures can comprise hardware, firmware and/or software, and can take any of a variety of form factors. Typical examples of such form factors include servers, laptops, smartphones, small form factor personal computers, personal digital assistants, and so on. The functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Illustrative examples of the disclosure include:

Aspect 1: A system comprising: a biosensor comprising at least one electrode to receive signals from a patient, an amplifier to receive the signals from the at least one electrode, an analog-to-digital converter to receive the signals from the amplifier and convert the signals to digital data, a microprocessor, and an antenna to transmit the digital data, and a mobile computing device having a memory storing computer-readable instructions, and at least one processor to execute the instructions to: illuminate at least one photostimulator of the mobile computing device to provide luminous stimulation to the patient and perform measurements associated with ocular/retinal functions of the patient, receive the digital data from the biosensor in response to the luminous stimulation, display a waveform associated with the measurements on a graphical user interface (GUI), perform a comparison between the measurements and a library of diagnostic images, and determine an evaluation of a retinal function of the patient based on the comparison.

Aspect 2: The system of Aspect 1, wherein the at least one electrode comprises a first electrode that makes electrical contact with the patient, a second electrode that is a ground electrode, and a third electrode that is a reference electrode.

Aspect 3: The system of any of Aspects 1 and 2, wherein the biosensor further comprises a coin battery to power the biosensor.

Aspect 4: The system of any of Aspects 1 to 3, wherein the measurements comprise electroretinography in response to the luminous stimulation less than a particular threshold in a dark-adapted eye of the patient.

Aspect 5: The system of any of Aspects 1 to 4, wherein the measurements comprise electroretinography in response to the luminous stimulation greater than or equal to a particular threshold in a dark-adapted eye of the patient.

Aspect 6: The system of any of Aspects 1 to 5, wherein the measurements comprise electroretinography in response to the luminous stimulation greater than or equal to a particular threshold in a light-adapted eye of the patient.

Aspect 7: The system of any of Aspects 1 to 6, wherein the measurements comprise electroretinography in response to the luminous stimulation that is repeated.

Aspect 8: The system of any of Aspects 1 to 7, the at least one processor further to determine that the patient has a retinal disorder based on the evaluation of the retinal function of the patient.

Aspect 9: The system of any of Aspects 1 to 8, wherein the retinal disorder comprises at least one of Retinitis pigmentosa, Retinitis pigmentosa sine pigmento, Retinitis punctata albescens, Leber's congenital amaurosis, Choroideremia, Gyrate atrophy of the retina and choroid, Goldman-Favre syndrome, Congenital stationary night blindness, X-linked juvenile retinoschisis, Achromatopsia, cone and dystrophies, and at least one disorder mimicking retinitis pigmentosa.

Aspect 10: The system of any of Aspects 1 to 9, wherein the biosensor and the mobile computing device communicate using BLUETOOTH Low Energy (BLE).

Aspect 11: The system of any of Aspects 1 to 10, wherein the measurements comprise at least one of a full-field flash electroretinography (ERG), a pattern ERG, a multi-focal ERG, an electrooculogram, and dark adaptation impairment.

Aspect 12: A method comprising illuminating, by at least one processor of a mobile computing device, at least one photostimulator of the mobile computing device to provide luminous stimulation to a patient and perform measurements associated with ocular/retinal functions of the patient, receiving, by at least one electrode of a biosensor, signals from the patient, receiving, by an amplifier of the biosensor, the signals from the at least one electrode, receiving, by an analog-to-digital converter of the biosensor, the signals from the amplifier and converting the signals to digital data, transmitting, by an antenna of the biosensor, the digital data to the mobile computing device, receiving, by the at least one processor of the mobile computing device, the digital data from the biosensor in response to the luminous stimulation, displaying, by the at least one processor of the mobile computing device, a waveform associated with the measurements on a graphical user interface (GUI), performing, by the at least one processor of the mobile computing device, a comparison between the measurements and a library of diagnostic images, and determining, by the at least one processor of the mobile computing device, an evaluation of a retinal function of the patient based on the comparison.

Aspect 13: The method of Aspect 12, wherein the at least one electrode comprises a first electrode that makes electrical contact with the patient, a second electrode that is a ground electrode, and a third electrode that is a reference electrode.

Aspect 14: The method of any of Aspects 12 and 13, wherein the biosensor further comprises a coin battery to power the biosensor.

Aspect 15: The method of any of Aspects 12 to 14, wherein the measurements comprise electroretinography in response to the luminous stimulation less than a particular threshold in a dark-adapted eye of the patient.

Aspect 16: The method of any of Aspects 12 to 15, wherein the measurements comprise electroretinography in response to the luminous stimulation greater than or equal to a particular threshold in a dark-adapted eye of the patient.

Aspect 17: The method of any of Aspects 12 to 16, wherein the measurements comprise electroretinography in response to the luminous stimulation greater than or equal to a particular threshold in a light-adapted eye of the patient.

Aspect 18: The method of any of Aspects 12 to 17, wherein the measurements comprise electroretinography in response to the luminous stimulation that is repeated.

Aspect 19: The method of any of Aspects 12 to 18, further comprising determining that the patient has a retinal disorder based on the evaluation of the retinal function of the patient.

Aspect 20: The method of any of Aspects 12 to 19, wherein the retinal disorder comprises at least one of Retinitis pigmentosa, Retinitis pigmentosa sine pigmento, Retinitis punctata albescens, Leber's congenital amaurosis, Choroideremia, Gyrate atophy of the retina and choroid, Goldman-Favre syndrome, Congenital stationary night blindness, X-linked juvenile retinoschisis, Achromatopsia, cone and dystrophies, and at least one disorder mimicking retinitis pigmentosa.

Aspect 21: The method of any of Aspects 12 to 20, wherein the biosensor and the mobile computing device communicate using BLUETOOTH Low Energy (BLE).

Aspect 22: The method of any of Aspects 12 to 21, wherein the measurements comprise at least one of a full-field flash electroretinography (ERG), a pattern ERG, a multi-focal ERG, an electrooculogram, and dark adaptation impairment.

Aspect 23: A non-transitory computer-readable storage medium comprising instructions stored thereon that, when executed by a mobile computing device cause the mobile computing device to perform operations, the operations including illuminating at least one photostimulator of the mobile computing device to provide luminous stimulation to a patient and perform measurements associated with ocular/retinal functions of the patient, receiving, by at least one electrode of a biosensor, signals from the patient, receiving, by an amplifier of the biosensor, the signals from the at least one electrode, receiving, by an analog-to-digital converter of the biosensor, the signals from the amplifier and converting the signals to digital data, transmitting, by an antenna of the biosensor, the digital data to the mobile computing device, receiving the digital data from the biosensor in response to the luminous stimulation, displaying a waveform associated with the measurements on a graphical user interface (GUI), performing a comparison between the measurements and a library of diagnostic images, and determining an evaluation of a retinal function of the patient based on the comparison.

What is claimed is:

1. A system comprising:

a biosensor comprising at least one electrode to receive signals from a patient, an amplifier to receive the signals from the at least one electrode, an analog-to-digital converter to receive the signals from the amplifier and convert the signals to digital data, a microprocessor, and an antenna to transmit the digital data;

a mobile computing device having a memory storing computer-readable instructions; and at least one processor to execute the instructions to:

in response to a selection on a first graphical user interface (GUI) on a touchscreen of the mobile computing device, illuminate at least one photostimulator of the mobile computing device to provide luminous stimulation directly from the mobile computing device to at least one eye of the patient and perform measurements associated with ocular/retinal functions of the patient, the measurements comprising an electrooculogram, the at least one photostimulator comprising one or more light emitting diode (LED) devices of the mobile computing device and one or more display devices of the mobile computing device;

receive the digital data from the biosensor in response to the luminous stimulation, the digital data communicated wirelessly from the biosensor to the mobile computing device;

display a waveform on the touchscreen of the mobile computing device associated with the measurements on a second GUI;

perform a comparison as the digital data is received wirelessly from the biosensor, the comparison based on the measurements and a library of diagnostic images; and determine an evaluation of a retinal function of the patient based on the comparison.

2. The system of claim 1, wherein the at least one electrode comprises a first electrode that makes electrical contact with the patient, a second electrode that is a ground electrode, and a third electrode that is a reference electrode.

3. The system of claim 1, wherein the biosensor further comprises a coin battery to power the biosensor.

4. The system of claim 1, wherein the measurements comprise electroretinography in response to the luminous stimulation less than a particular threshold in a dark-adapted eye of the patient.

5. The system of claim 1, wherein the measurements comprise electroretinography in response to the luminous stimulation greater than or equal to a particular threshold in a dark-adapted eye of the patient.

6. The system of claim 1, wherein the measurements comprise electroretinography in response to the luminous stimulation greater than or equal to a particular threshold in a light-adapted eye of the patient.

7. The system of claim 1, wherein the measurements comprise electroretinography in response to the luminous stimulation that is repeated.

8. The system of claim 1, the at least one processor further to determine that the patient has a retinal disorder based on the evaluation of the retinal function of the patient, wherein the comparison is based on the measurements and the library of diagnostic images stored locally on the mobile computing device, the library of diagnostic images having images associated with retinal functions from people other than the patient.

9. The system of claim 8, wherein the retinal disorder comprises at least one of Retinitis pigmentosa, Retinitis pigmentosa sine pigmento, Retinitis punctata albescens, Leber's congenital amaurosis, Choroideremia, Gyrate atophy of the retina and choroid, Goldman-Favre syndrome, Congenital stationary night blindness, X-linked juvenile retinoschisis, Achromatopsia, cone-rod dystrophies, and at least one disorder mimicking retinitis pigmentosa.

10. The system of claim 1, wherein the biosensor and the mobile computing device communicate using a low energy communication protocol.

11. The system of claim 1, wherein the measurements further comprise at least one of a full-field flash electroretinography (ERG), a pattern ERG, a multi-focal ERG, and dark adaptation impairment.

12. A method, comprising:

in response to a selection on a first graphical user interface (GUI) on a touchscreen of a mobile computing device, illuminating, by at least one processor of the mobile computing device, at least one photostimulator of the mobile computing device to provide luminous stimulation directly from the mobile computing device to at least one eye of a patient and perform measurements associated with ocular/retinal functions of the patient, the measurements comprising an electrooculogram, the at least one photostimulator comprising one or more light emitting diode (LED) devices of the mobile computing device and one or more display devices of the mobile computing device;

receiving, by at least one electrode of a biosensor, signals from the patient;

receiving, by an amplifier of the biosensor, the signals from the at least one electrode;

receiving, by an analog-to-digital converter of the biosensor, the signals from the amplifier and converting the signals to digital data;

transmitting, by an antenna of the biosensor, the digital data to the mobile computing device;

receiving, by the at least one processor of the mobile computing device, the digital data from the biosensor in response to the luminous stimulation, the digital data communicated wirelessly from the biosensor to the mobile computing device;

displaying, by the at least one processor of the mobile computing device, a waveform on the touchscreen of the mobile computing device associated with the measurements on a second GUI;

performing, by the at least one processor of the mobile computing device, a comparison as the digital data is received wirelessly from the biosensor, the comparison based on the measurements and a library of diagnostic images; and determining, by the at least one processor of the mobile computing device, an evaluation of a retinal function of the patient based on the comparison.

13. The method of claim 12, wherein the at least one electrode comprises a first electrode that makes electrical contact with the patient, a second electrode that is a ground electrode, and a third electrode that is a reference electrode.

14. The method of claim 12, wherein the biosensor further comprises a coin battery to power the biosensor.

15. The method of claim 12, wherein the measurements comprise electroretinography in response to the luminous stimulation less than a particular threshold in a dark-adapted eye of the patient.

16. The method of claim 12, wherein the measurements comprise electroretinography in response to the luminous stimulation greater than or equal to a particular threshold in a dark-adapted eye of the patient.

17. The method of claim 12, wherein the measurements comprise electroretinography in response to the luminous stimulation greater than or equal to a particular threshold in a light-adapted eye of the patient.

18. The method of claim 12, wherein the measurements comprise electroretinography to in response the luminous stimulation that is repeated.

19. The method of claim 12, further comprising determining that the patient has a retinal disorder based on the evaluation of the retinal function of the patient, wherein the comparison is based on the measurements and the library of diagnostic images stored locally on the mobile computing device, the library of diagnostic images having images associated with retinal functions from people other than the patient.

20. The method of claim 19, wherein the retinal disorder comprises at least one of Retinitis pigmentosa, Retinitis pigmentosa sine pigmento, Retinitis punctata albescens, Leber's congenital amaurosis, Choroideremia, Gyrate atophy of the retina and choroid, Goldman-Favre syndrome, Congenital stationary night blindness, X-linked juvenile retinoschisis, Achromatopsia, cone-rod dystrophies, and at least one disorder mimicking retinitis pigmentosa.

21. The method of claim 12, wherein the biosensor and the mobile computing device communicate using a low energy communication protocol.

22. The method of claim 12, wherein the measurements further comprise at least one of a full-field flash electroretinography (ERG), a pattern ERG, a multi-focal ERG, and dark adaptation impairment.

23. A non-transitory computer-readable storage medium comprising instructions stored thereon that, when executed by a mobile computing device cause the mobile computing device to perform operations, the operations comprising:

in response to a selection on a first graphical user interface (GUI) on a touchscreen of the mobile computing device, illuminating at least one photostimulator of the mobile computing device to provide luminous stimulation directly from the mobile computing device to at least one eye of a patient and perform measurements associated with ocular/retinal functions of the patient, the measurements comprising an electrooculogram, the at least one photostimulator comprising one or more light emitting diode (LED) devices of the mobile computing device and one or more display devices of the mobile computing device;

receiving, by at least one electrode of a biosensor, signals from the patient;

receiving, by an amplifier of the biosensor, the signals from the at least one electrode;

receiving, by an analog-to-digital converter of the biosensor, the signals from the amplifier and converting the signals to digital data;

transmitting, by an antenna of the biosensor, the digital data to the mobile computing device;

receiving the digital data from the biosensor in response to the luminous stimulation, the digital data communicated wirelessly from the biosensor to the mobile computing device;

displaying a waveform on the touchscreen of the mobile computing device associated with the measurements on a second GUI;

performing a comparison as the digital data is received wirelessly from the biosensor, the comparison based on the measurements and a library of diagnostic images; and determining an evaluation of a retinal function of the patient based on the comparison.

* * * * *